United States Patent [19]
Foss et al.

[11] Patent Number: 5,972,954
[45] Date of Patent: Oct. 26, 1999

[54] USE OF METHYLNALTREXONE AND RELATED COMPOUNDS

[75] Inventors: Joseph F. Foss; Michael F. Roizen; Jonathan Moss; Chun-Su Yuan, all of Chicago, Ill.; William Drell, San Diego, Calif.

[73] Assignees: Arch Development Corporation, Chicago, Ill.; UR Labs, Inc., Reno, Nev.

[21] Appl. No.: 08/962,742

[22] Filed: Nov. 3, 1997

[51] Int. Cl.$^6$ .................................................. A61K 31/485
[52] U.S. Cl. .............................................................. 514/282
[58] Field of Search ............................................. 514/282

[56] References Cited

U.S. PATENT DOCUMENTS 4,176,186  11/1979  Goldberg et al. ........................ 424/260

OTHER PUBLICATIONS

Yuan et al., Clin. Pharmacol. Ther., 59(4), 469–475 (abstract), 1996.
Yuan, Chun Su et al., *European Journal of Pharmacology*, 276:107–111, 1995.
Yuan, Chun Su et al., *Clinical Pharmacology & Therapeutics*, 61:467–75, 1997.
Foss, Joseph F., *The Journal of Clinical Pharmacology*, 1997;37:25–30.
Yuan, Chun Su et al., *Clinical Pharmacology & Therapeutics*, 59:469–75, 1996.

*Primary Examiner*—Phyllis G. Spivack
*Attorney, Agent, or Firm*—Christie, Parker & Hale, LLP

[57] ABSTRACT

A method for preventing or treating opioid induced side effects including dysphoria, pruritus and urinary retention and non-opioid induced changes in gastrointestinal motility. The method comprises administering methylnaltrexone or another quaternary derivative of noroxymorphone to a patient prior to the administration of an opioid or after the onset of side effects induced by the administration of an opioid, wherein the methylnaltrexone or quaternary derivative is administered by the route selected from the group consisting of intravenous, intramuscular, transmucosal, transdermal, and oral administration, preferably administered orally in an enterically coated form.

46 Claims, No Drawings

USE OF METHYLNALTREXONE AND RELATED COMPOUNDS

FIELD OF THE INVENTION

The present invention is directed at the treatment of certain side effects associated with the use of opioids as analgesics. In particular the present invention is directed at treating opioid-induced dysphoria, opioid-induced pruritus, opioid-induced urinary retention, inhibition of gastric emptying, and decreased gut motility.

BACKGROUND OF THE INVENTION

Opioids are effective analgesics, however, their use is associated with a number of undesirable side effects. One of these side effects is pruritus, or itching. Pruritus is a common side effect associated with the use of opioids and may be very severe. Pruritus can occur when the opioid is administered intramuscularly, intravenously, transdermally, transmucosally or intrathecally.

It is believed that the opioid induced pruritus results from the release of histamine in response to the administration of opioids. Opioids are thought to stimulate histamine release by binding to opioid receptors on the central nervous system. This, in turn, causes peripheral nerves and histamine containing cells to release histamine.

Based on this theory a number of treatments have been used to alleviate opioid induced pruritus. The first is the use of antihistamines. However, antihistamines have a variable effect on opioid induced pruritus. Additionally, the use of antihistamines, when effective, only treats the symptom after it has occurred, rather than preventing its occurrence.

Another undesirable side effect of opioids is urinary retention, or the patient's inability to spontaneously empty his or her bladder. This urinary retention is a common side effect that can occur when opioids or related compounds are administered intramuscularly, intravenously, transmucosally, transdermally, or intrathecally. It is not clear why opioids cause urinary retention, but it is thought to be related to the central anticholinergic stimulation that opioids induce. Based on this theory, a number of cholinergic-type drugs have been used to treat urinary retention. However, due to the side effects of cholinergic drugs, catheterization of the bladder with a tube to drain urine remains the mainstay of treatment.

Another opioid-induced side effect is dysphoria, a feeling of unpleasantness or discomfort. Many subjects, especially those without pain, report unpleasant psychomimetic responses to the administration of an opioid alone. These responses have been previously attributed to activation of centrally located opioid receptors. This opioid-induced dysphoria is commonly treated by the addition of other drugs, such as benzodiazepines, to decrease the dysphoria or to blunt the recall of the dysphoria. These drugs, however are associated with increased levels of sedation and may enhance respiratory depression caused by the opioid.

One treatment for side effects such as pruritis, urinary retention and dysphoria is the use of opioid antagonists which cross the blood-brain-barrier, or which are administered directly into the central nervous system. Opioid antagonists such as naltrexone and naloxone have been administered intramuscularly or orally to treat opioid induced pruritus. Naltrexone and naloxone are highly lipid soluble and rapidly diffuse across biological membranes, including the blood-brain-barrier. However, naltrexone, naloxone and other opioid antagonists also reduce the analgesic effect of the opioid being used.

Many quaternary amine opioid antagonist derivatives, such as methylnaltrexone, do not reduce the analgesic effect of the opioids. These quaternary amine opioid antagonist derivatives, which have a relatively higher polarity and reduced lipid solubility when compared to the tertiary forms of the drugs, were specifically developed to not traverse the blood-brain-barrier or to traverse it at a greatly reduced rate. Since these quaternary opioid antagonist derivatives do not cross the blood-brain-barrier, peripheral administration of these antagonists would not be expected to be effective in the treatment of an opioid induced side effect caused by the opioid within the central nervous system. In fact, experiments show that to be effective in blocking the opioid receptors in the central nervous system, these antagonists must be injected directly into the central nervous system. However, injection of drugs directly into the central nervous system is undesirable since it increases the possibility of introducing bacterial or viral contamination to the central nervous system.

It is desirable in the treatment of many conditions to have oral medications with prolonged effects. Such oral medications are particularly desirable both for the treatment of opioid-induced side effects (such as urinary retention, pruritus, and some forms of constipation) and for the treatment of nonopioid-induced side effects (such as other forms of constipation and delayed gastric emptying from enteric feeding).

It is further desirable to develop a method for the prevention of opioid induced dysphoria, opioid induced pruritus, urinary retention, opioid- or nonopioid-induced delayed gastric emptying from enteric feeding, and constipation, which does not counteract the analgesic effects of the opioid, or risk increased levels of pain.

SUMMARY OF THE INVENTION

The present invention is directed at methods for preventing and treating opioid-induced pruritus, opioid-induced urinary retention, opioid- or nonopioid-induced inhibition of gastric emptying by enteric feeding, and opioid- or nonopioid-induced constipation.

The method for preventing opioid-induced side effects, including dysphoria, pruritus, urinary retention, inhibition of gastric emptying by enteric feeding, and constipation, comprises administering methylnaltrexone or enteric coated methylnaltrexone, or other quaternary derivatives of noroxymorphone as disclosed in U.S. Pat. No. 4,176,186 to Goldberg et al. (herein incorporated by reference) to a patient prior to the administration of an opioid wherein the route of administration is selected from the group consisting of intravenous, intramuscular, intraperitoneal, transmucosal, transdermal, and oral administration in a standard or enterically coated preparation.

The method for treating opioid-induced side effects, including dysphoria, pruritus, urinary retention, inhibition of gastric emptying by enteric feeding, and constipation, comprises administering methylnaltrexone or enteric coated methylnaltrexone, or other quaternary derivatives of noroxymorphone, to a patient after the onset of the side effect, wherein the route of administration is selected from the group consisting of intravenous, intramuscular, transmucosal, transdermal and oral administration in a standard or enterically coated preparation.

The method for preventing nonopioid-induced side effects of opioid administration, including gastrointestinal dysfunction (e.g., inhibition of gastric emptying by enteric feeding and constipation), comprises administering methylnaltrexone or enteric coated methylnaltrexone, or other quaternary derivatives of noroxymorphone, to a patient prior to the development of the side effects wherein the route of administration is selected from the group consisting of intravenous, intramuscular, transmucosal, transdermal and oral administration in a standard or enterically coated preparation.

The method for treating nonopioid-induced side effects, including inhibition of gastric emptying by enteric feeding and constipation, comprises administering methylnaltrexone or enteric coated methylnaltrexone, or other quaternary derivatives of noroxymorphone, to a patient after the onset of the side effect, wherein the route of administration is selected from the group consisting of intravenous, intramuscular, transmucosal, transdermal and oral administration in a standard or enterically coated preparation.

DETAILED DESCRIPTION

The present invention is directed at methods for preventing and treating opioid-induced dysphoria, opioid-induced pruritus, opioid-induced urinary retention, opioid- or nonopioid-induced inhibition of gastric emptying by enteric feeding, and opioid- or nonopioid-induced constipation. When used as a treatment for these opioid- and nonopioid-induced side effects, orally administered, particularly if enteric coated, methylnaltrexone (MNTX) or other quaternary derivatives of noroxymorphone (QDMN) provides prolonged relief of the side effects. Furthermore, for treatment or prevention of delayed gastric emptying from enteric feeding and constipation, whether caused by extrinsic or endogenous opioids, enteric coating surprisingly allows for equal or better efficacy despite lower plasma levels. Idiopathic constipation, i.e., that due to causes other than exogenous administration of opioids, may be mediated by opioid sensitive mechanisms. Endogenous opioid receptors have been identified in the gut, and these receptors may modulate gut motility. Thus, administration of an opioid antagonist with peripheral action, such a methylnaltrexone or other quaternary derivatives of noroxymorphone, would block the effects of endogenous opioids.

Quaternary derivatives of noroxymorphone are described in full in Goldberg et al., (supra), and in general are represented by the formula:

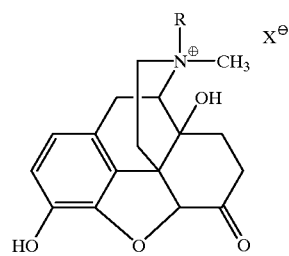

wherein R is allyl or a related radical such as chlorallyl, cyclopropyl-methyl or propargyl, and X is the anion of an acid, especially a chloride, bromide, iodide or methylsulfate anion.

The presently preferred quaternary derivative of noroxymorphone is methylnaltrexone. Methylnaltrexone is a quaternary amine derivative of naltrexone. Methylnaltrexone has been found to have only 2 to 4% of the opiate antagonistic activity of naltrexone in vivo due to its inability to pass the blood-brain-barrier and bind to the opiate receptors in the central nervous system.

Opioids are typically administered at a morphine equivalent dosage of: 0.005 to 0.15 mg/kg body weight for intrathecal administration; 0.05 to 1.0 mg/kg body weight for intravenous administration; 0.05 to 1.0 mg/kg body weight for intramuscular administration; 0.05 to 1.0 mg/kg body weight/hour for transmucosal or transdermal administration. By "morphine equivalent dosage" is meant representative doses of other opioids which equal one milligram of morphine, for example 10 mg meperidine, 1 mg methadone, and 80 µg fentanyl.

In accordance with the present invention, methylnaltrexone is administered at a dosage of: 0.03 to 1.0 mg/kg body weight for intravenous administration; 0.03 to 1.0 mg/kg body weight for intramuscular administration; 0.03 to 1.0 mg/kg body weight for transmucosal administration and 1.0 to 40.0 mg/kg body weight for oral administration. In accordance with the present invention, enteric coated methylnaltrexone, is administered at a dosage of 1.0 to 80.0 mg/kg body weight for oral administration.

The administration of the methylnaltrexone is preferably commenced prior to administration of the opioid to prevent opioid-induced dysphoria, pruritus, urinary retention, inhibition of gastric emptying with enteric feeding, or constipation. It is desirable to commence administration of methylnaltrexone about 5 minutes for parenteral MNTX administration and 20 minutes for enteral MNTX administration prior to administration of opioids in order to prevent these opioid-induced side effects. It is also preferable to administer the methylnaltrexone prior to the onset of nonopioid-induced gastric dysfunction symptoms, inhibition of gastric emptying with enteric feeding or constipation, in order to prevent these symptoms from manifesting. While the prevention of symptoms is preferred, methylnaltrexone administration may also be commenced after the administration of the opioid or after the onset of opioid induced symptoms as a treatment for those symptoms.

Methylnaltrexone is rapidly absorbed after oral administration from the stomach and bowel. Initial plasma levels of the drug are seen within 5–10 minutes of the administration of non-enteric coated compound. Addition of an enteric coating which prevents gastric absorption is associated with lower plasma levels of the methylnaltrexone. Surprisingly, the addition of an enteric coating (i.e., a coating which will prevent degradation or release in the stomach, but will release drug in the small and large bowel) appears to enhance the efficacy of methylnaltrexone in the prevention of decreases in gut motility by intravenously administered opioids (morphine).

For intravenous administration, methylnaltrexone is formulated with saline or other physiologically acceptable carriers; for intramuscular administration, the methylnaltrexone is formulated with saline or other pharmacologically acceptable carriers; for transmucosal administration the methylnaltrexone is formulated with a sugar and cellulose mix or other pharmacologically acceptable carriers known in the art; and for oral administration, the methylnaltrexone is formulated with pharmacologically acceptable binders to make a tablet or capsule with or without an enteric coating. Methods for such formulations are well known to those skilled in the art.

In a preferred embodiment for the prevention and/or treatment of constipation, the MNTX is enterically coated and administered orally.

The enteric coating may be made of any suitable composition. Suitable enteric coatings are described, for example, in U.S. Pat. Nos. 4,311,833 to Namikoshi, et al.; 4,377,568 to Chopra; 4,385,078 to Onda, et al.; 4,457,907 to Porter;

4,462,839 to McGinley, et al.; 4,518,433 to McGinley, et al.; 4,556,552 to Porter, et al.; 4,606,909 to Bechgaard et al.; 4,615,885 to Nakagame, et al.; 4,670,287 to Tsuji; 5,536,507 TO Abramowitz, et al.; 5,567,423 to Ying, et al.; 5,591,433 to Michael, et al.; 5,597,564 to Ying, et al.; 5,609,871 to Michael, et al.; 5,614,222 to Kaplan; 5,626,875 to Rodes, et al.; and 5,629,001 to Michael, et al., all of which are incorporated herein by reference.

Preferred enteric coating compositions include alkyl and hydroxyalkyl celluloses and their aliphatic esters, e.g., methylcellulose, ethylcellulose, hydroxyethylcellulose, hydroxypropylcellulose, hydroxybutylcellulose, hydroxyethylethylcellulose, hydroxyprophymethylcellulose, hydroxybutylmethylcellulose, hydroxypropylcellulose phthalate, hydroxypropylmethylcellulose phthalate and hydroxypropylmethylcellulose acetate succincate; carboxyalkylcelluloses and their salts, e.g., carboxymethylethylcellulose; cellulose acetate phthalate; cellulose acetate trimellitate, polycarboxymethylene and its salts and derivatives; polyvinylalcohol and its esters: polyvinyl acetate phthalate; polycarboxymethylene copolymer with sodium formaldehyde carboxylate; acrylic polymers and copolymers, e.g., methacrylic acid-methyl methacrylic acid copolymer and methacrylic acid-methyl acrylate copolymer; edible oils such as peanut oil, palm oil, olive oil and hydrogenated vegetable oils; polyvinylpyrrolidone; polyethyleneglycol and its esters: natural products such as shellac, and zein.

Other preferred enteric coatings include polyvinylacetate esters, e.g., polyvinyl acetate phthalate; alkyleneglycolether esters of copolymers such as partial ethylene glycol monomethylether ester of ethylacrylate-maleic anhydride copolymer or diethyleneglycol monomethylether ester of methylacrylate-maleic anhydride copolymer, N-butylacrylate-maleic anhydride copolymer, isobutylacrylate-maleic anhydride copolymer or ethylacrylate-maleic anhydride copolymer; and polypeptides resistant to degradation in the gastric environment, e.g., polyarginine and polylysine.

Mixtures of two or more of the above compounds may be used as desired. The presently preferred enteric coating comprises cellulose acetate phthalate.

The enteric coating material may be mixed with various excipients including plasticizers such as triethyl citrate, acetyl triethyl citrate, diethyl phthalate, dibutyl phthalate, dibutyl subacute, dibutyl tartrate, dibutyl maleate, dibutyl succinate and diethyl succinate and inert fillers such as chalk or pigments.

The composition and thickness of the enteric coating may be selected to dissolve immediately upon coated with the digestive juice of the intestine. Alternatively, the composition and thickness of the anterior coating may be selected to be a time-release coating which dissolves over a selected period of time, as is well known in the art.

The amount of enteric coating depends on the particular enteric coating composition used and is preferably sufficient to substantially prevent the absorption of MNTX in the stomach.

Hydroxyalkyl celluloses and their aliphatic esters, carboxyalkyl celluloses and their salts, polycarboxymethylene and its salts and derivatives, polyvinyl alcohol and its esters, polycarboxymethylene copolymer with sodium formaldehyde carboxylates, poly-vinylpyrrolidone, and polyethylene glycol and its esters can be applied as enteric coatings by first dissolving the compound in a minimum amount of water. Alcohol is then added to the point of incipient cloudiness. The mixture can then be applied by conventional techniques.

Application of cellulose acetate phthalate may be accomplished by simply dissolving the cellulose acetate phthalate in a minimum amount of alcohol and then applying by conventional techniques. Hydrogenated vegetable oils may be applied by first dissolving the oil in a minimal amount of a non-polymer solvent, such as methylene chloride, chloroform or carbon tetrachloride, then adding alcohol to the point of incipient cloudiness and then applying by conventional techniques.

In a particularly preferred embodiment, the MNTX is coated with Eudragit L100 or S100, a methacrylic acid copolymer enteric coating, at a 50% coating level to provide stability at gastric pH and dissolution at gut pH per a US Pharmacopeia (USP) standard for enteric coatings.

Any art-known transdermal application may be used, but transdermal administration is preferably via a patch applied to the skin with a membrane of sufficient permeability to allow diffusion of MNTX at a fixed rate in the range of 1.0 to 10.0 mg/hr. The rate of administration may be varied by varying the size of the membrane contact area and/or applying an electrical wiring potential to a drug reservoir. The patch preferably holds 25 mg to 1 gram of available drug in the reservoir plus additional drug as needed for the mechanics of the system.

In the above description, methylnaltrexone is used as an example of a particularly effective QDNM. It is apparent that other QDNM's may be used as desired.

The following Examples are intended to illustrate aspects of the invention and are not to be construed as limitations upon it. The methylnaltrexone used in the following Examples was manufactured by Mallinckrodt Pharmaceuticals, St. Louis, Mo. The Enteric Coating was manufactured by Coating Place, Inc., Verona, Wis.

EXAMPLE 1

Ten patients were treated with morphine sulfate administered directly to the central nervous system or intravenously. The morphine sulfate was administered at 0.1 mg/kg body weight. The patients in the study had been treated for pain resulting from surgery. All the patients exhibited pruritus as a side effect of the morphine sulfate administration. Subsequent to the onset of the pruritus, methylnaltrexone, at a dosage of 0.3 mg/kg of body weight was administered intravenously as a saline solution containing methylnaltrexone in a concentration of 5 mg/ml to each of the patients. Eighty percent of the 10 patients exhibited relief from the pruritus sixty minutes after receiving methylnaltrexone.

In a control group, 8 patients were treated with morphine sulfate administered directly to the central nervous system or intravenously. The morphine sulfate was administered at 0.1 mg/kg body weight. The patients in the study had been treated for pain resulting from surgery. All the patients exhibited pruritus as a side effect of the morphine sulfate administration. A placebo, saline at a volume equivalent to the volume administered to patients receiving active drug, was administered intravenously to each of the patients. Only 50% of the patients exhibited relief from the pruritus within sixty minutes.

The study indicates that methylnaltrexone was effective in treating pruritus induced by morphine sulfate.

EXAMPLE 2

Efficacy of Enteric Coating of Methylnaltrexone

Morphine (0.05) mg/kg intravenous) was administered to three volunteers after the oral administration of placebo, methylnaltrexone (6.4 mg/kg) in a gelatin capsule (which dissolves readily in the stomach), or methylnaltrexone after enteric coating (12.8 mg/kg of substance to yield a mass of 6.4 mg/kg methylnaltrexone incorporated) which has decreased release and absorption in the stomach. Oral-cecal transit time was measured using the lactulose-hydrogen breath test. Plasma levels of methylnaltrexone were measured and after the enteric coated preparation were lower. In each subject morphine alone increased the oral-cecal transit time by 20–70 minutes, methylnaltrexone blocked this effect, and enteric coated methylnaltrexone blocked the effect to a similar or greater extent than the uncoated methylnaltrexone.

EXAMPLE 3

Enhancement of Enteric Feeding

Two patients receiving morphine (375 mg/day and 18 mg/day) and receiving enteric tube feedings of 200 ml every four (4) hours were studied. The first patient had residual stomach contents of 50 cc to 100 cc, or 22.0–58.8% of administered feedings measured every 4 hours during a 24 hour control period. Prior to drug administration the residual volume had increased to 260 cc or >100% of previous feeding volume. Methylnaltrexone, 0.45 mg/kg, was administered intravenously every 4 hours for 24 hours, after the control period. After the first dose (4 hours) of MNTX, the residual was 150 cc or 58% of the previous bolus feed, after the 3rd dose (12 hours) the residual was 75 cc or 30% of the previous feed, after the 5th dose (20 hours) the residual was 22 cc or 13% of the previous feed and after the 6th and final dose (24 hours) the residual was 8 cc or 5.5% of previous feed. The follow-up residual sampling after the final drug-tube feed interval had increased to 50 cc or 38% or previous feed.

The second patient had greater than 200 cc residual or 100% of previous feedings on two consecutive samplings, that is 8 hrs and 4 hrs before drug administration. After initiation of Methylnaltrexone, 0.45 mg/kg, administered intravenously every 4 hours, the first residual (4 hrs) was 0 cc, the second residual (8 hrs)was 24 cc or 15% of previous bolus feed.

EXAMPLE 4

Treatment of Urinary Retention

Subjects receiving morphine at a variety of doses (via patient controlled analgesia—PCA) who experience urinary retention are administered Methylnaltrexone 0.45 mg/kg intravenously or a placebo. Those treated with Methylnaltrexone have resolution of their symptoms, while those administered placebo go on to require additional therapy (usually urinary catheterization).

EXAMPLE 5

In a double-blind randomized placebo-controlled study, we evaluated the efficacy of oral methylnaltrexone to decrease subjective effects after administering morphine to 10 normal human volunteers. After intravenous morphine injection (0.05 mg/kg), significant increases in subjective ratings were obtained on "nauseous", "skin itch", "stimulated", and "flushing". Compared to baseline, significant increases were obtained on "nauseous", "skin itch", "stimulated", and "flushing" ratings after placebo and morphine administration ($P<0.05$, $P<0.05$, $P<0.01$ and $P<0.01$, respectively). Oral methylnaltrexone (19.2 mg/kg) significantly decreased these four ratings ($P<0.05$, $P<0.05$, $P<0.01$ and $P<0.01$, respectively) compared to placebo and morphine and resulted in no change when compared to baseline. Plasma methylnaltrexone concentrations were also measured and correlation between pharmacological effects of the compound and its plasma levels was shown. Our results indicate that methylnaltrexone decreases dysphoria and some other undesirable subjective effects associated with opioid medications.

The preceding description and Examples are intended to be illustrative. Those skilled in the art to which the invention pertains will appreciate that alterations and changes in the described protocols may be practiced without departing from the meaning, spirit, and scope of this invention. Therefore, the foregoing description should be read consistent with and as support to the following claims, which are to have their fullest and fair scope.

What is claimed is:

1. A method for preventing opioid induced side effects comprising administering a quaternary derivative of noroxymorphone to a patient prior to the administration of an opioid, the side effect selected from the group consisting of dysphoria, pruritus, and urinary retention.

2. The method as recited in claim 1 wherein the quaternary derivative is methylnaltrexone.

3. The method as recited in claim 2 wherein the methylnaltrexone is administered by the route selected from the group consisting of intravenous, intramuscular, transmucosal, transdermal, and oral administration.

4. The method as recited in claim 3 wherein the methylnaltrexone is formulated with saline for administration by the route selected from the group comprising intravenous and intramuscular administration.

5. The method as recited in claim 3 wherein the methylnaltrexone is formulated with a sugar and cellulose mix for transmucosal administration.

6. The method as recited in claim 3 wherein the methylnaltrexone is formulated with binders to make a tablet for oral administration.

7. The method as recited in claim 6 wherein the tablet is coated with an enteric coating.

8. The method as recited in claim 6 wherein the methylnaltrexone is administered orally as an enterically coated tablet at a dosage of about 1.0 to about 80 mg/kg body weight.

9. The method as recited in claim 3 wherein the methylnaltrexone is administered at a dosage of about 0.03 to about 1.0 mg/kg body weight through a route selected from the group consisting of intravenous or intramuscular administration.

10. The method as recited in claim 3 wherein the methylnaltrexone is administered transmucosally at a dosage of about 0.03 to about 1.0 mg/kg body weight.

11. The method of claim 3 wherein the methylnaltrexone is administered transdermally at a dosage of about 1.0 to about 10.0 mg/kg body weight.

12. The method as recited in claim 3 wherein the methylnaltrexone is administered orally at a dosage of about 1.0 to about 40 mg/kg body weight.

13. The method as recited in claim 2 wherein the methylnaltrexone is formulated with a pharmacologically acceptable carrier.

14. The method as recited in claim 2 wherein the methylnaltrexone is administered at a dosage 0.03 to 1.0 mg/kg body weight for intravenous or intramuscular administration; 1.0 to 10.0 mg/kg for transdermal administration; 1.0 to 40.0 mg/kg body weight for administration of a methylnaltrexone tablet; and 1.0 to 80.0 mg/kg body weight for oral administration of an enterically coated methylnaltrexone tablet.

15. The method as recited in claim 1 wherein the side effect is dysphoria.

16. The method as recited in claim 1 wherein the side effect is pruritus.

17. The method as recited in claim 1 wherein the side effect is urinary retention.

18. A method for treating opioid induced side effects comprising administering a quaternary derivative of noroxymorphone to a patient subsequent to the administration of an opioid, the side effect selected from the group consisting of dysphoria, pruritus, and urinary retention.

19. The method of claim 18 wherein the quaternary derivative is methylnaltrexone.

20. The method as recited in claim 18 wherein the methylnaltrexone is administered by the route selected from the group consisting of intravenous, intramuscular, transmucosal, transdermal, and oral administration.

21. The method as recited in claim 20 wherein the methylnaltrexone is formulated with saline for administration by the route selected from the group comprising intravenous and intramuscular administration.

22. The method as recited in claim 20 wherein the methylnaltrexone is formulated with a sugar and cellulose mix for transmucosal administration.

23. The method as recited in claim 20 wherein the methylnaltrexone is formulated with binders to make a tablet for oral administration.

24. The method as recited in claim 23 wherein the tablet is coated with an enteric coating.

25. The method as recited in claim 23 wherein the methylnaltrexone is administered orally at a dosage of about 1.0 to about 40 mg/kg body weight.

26. The method as recited in claim 20 wherein the methylnaltrexone is administered at a dosage of about 0.03 to about 1.0 mg/kg body weight through a route selected from the group consisting of intravenous or intramuscular administration.

27. The method as recited in claim 20 wherein the methylnaltrexone is administered transmucosally at a dosage of about 0.03 to about 1.0 mg/kg body weight.

28. The method as recited in claim 20 wherein the methylnaltrexone is administered transdermally at a dosage of about 1.0 to about 10.0 mg/kg body weight.

29. The method as recited in claim 18 wherein the methylnaltrexone is formulated with a pharmacologically acceptable carrier.

30. The method as recited in claim 18 wherein the side effect is dysphoria.

31. The method as recited in claim 18 wherein the side effect is pruritus.

32. The method as recited in claim 18 wherein the side effect is urinary retention.

33. A method for preventing nonopioid induced gastrointestinal dysfunction comprising administering a quaternary derivative of noroxymorphone to a patient prior to the onset of the gastrointestinal dysfunction.

34. The method of claim 33 wherein the quaternary derivative is methylnaltrexone.

35. The method as recited in claim 34 wherein the methylnaltrexone is administered by the route selected from the group consisting of intravenous, intramuscular, transmucosal, transdermal, and oral administration.

36. The method as recited in claim 34 wherein the methylnaltrexone is formulated with binders to make a tablet, said tablet being coated with an enteric coating.

37. The method as recited in claim 34 wherein the methylnaltrexone is administered orally at a dosage of 1.0 to 80 mg/kg body weight.

38. The method as recited in claim 33 wherein the gastrointestinal dysfunction is selected from the group consisting of inhibition of gastric emptying and constipation.

39. A method for treating nonopioid induced gastrointestinal dysfunction comprising administering a quaternary derivative of noroxymorphone to a patient after the onset of the gastrointestinal dysfunction.

40. The method of claim 38 wherein the quaternary derivative is methylnaltrexone.

41. The method as recited in claim 40 wherein the methylnaltrexone is administered by the route selected from the group consisting of intravenous, intramuscular, transmucosal, transdermal, and oral administration.

42. The method as recited in claim 40 wherein the methylnaltrexone is formulated with binders to make a tablet said tablet being coated with an enteric coating.

43. The method as recited in claim 40 wherein the methylnaltrexone is administered orally at a dosage of 1.0 to 40 mg/kg body weight.

44. The method as recited in claim 39 wherein the gastrointestinal dysfunction is selected from the group consisting of inhibition of gastric emptying and constipation.

45. A method for preventing opioid induced dysphoria comprising administering a quaternary derivative of noroxymorphone to a patient prior to the administration of an opioid.

46. A method for treating opioid induced dysphoria comprising administering a quaternary derivative of noroxymorphphone to a patient subsequent to the administration of an opioid.

* * * * *